United States Patent [19]
Robinson

[11] Patent Number: 6,022,730
[45] Date of Patent: Feb. 8, 2000

[54] METHODS FOR THE ISOLATION OF BACTERIA CONTAINING EUKARYOTIC GENES

[76] Inventor: Douglas H. Robinson, 2301 N St., NW., Apt. 507, Washington, D.C. 20037

[21] Appl. No.: 08/719,367

[22] Filed: Sep. 25, 1996

Related U.S. Application Data

[63] Continuation-in-part of application No. 08/261,977, Jun. 17, 1994.

[51] Int. Cl.$^7$ .............................. C12Q 1/04; C12N 5/16; C12N 5/08
[52] U.S. Cl. ..................... 435/252.3; 435/34; 435/71.1; 435/240.2; 435/252.1
[58] Field of Search .................................. 435/240.2, 34, 435/252.1, 252.3, 71.1

[56] References Cited

U.S. PATENT DOCUMENTS

| | | |
|---|---|---|
| 4,695,543 | 9/1987 | Sloma et al. . |
| 4,868,111 | 9/1989 | Bujard et al. . |

FOREIGN PATENT DOCUMENTS 9012867  11/1990  WIPO .

OTHER PUBLICATIONS

Glover et al. The Canada Lancet & Practioner, Feb. 1926 pp. 49–62.
Weiss et al. ed. "RNA Tumor Viruses", CSH, 1985, p. 357–408.
Barron's Law Dictionary 3rd Ed., Steven H. Gifis, 1991, Barron's Educational Series, Inc., New York, p. 130.
Webster's II New Riverside University Dictionary, New Riverside Publishing Co., 1988.
Seibert et al. (A) J. of the Reticuloendothelial. Soc. 21(4):279–283, 1977.
Macomber et al. Med. Hypothesis (England) 32(1):1–9, 1990.
Seibert et al, (B) Annals New York Academy of Sciences 141:175–201, 1967.
Seibert et al. (C) Transactions New York Academy of Sciences series 11, vol. 34: 504–532, 1972.
Livingston et al. Ann. N.Y. Acad. Sci. vol. 174:636–654, 1970.
Diller et al. Ann. N.Y. Acad. Sci. vol. 174:655–674m 1970.
Acevedo et al. J. Gen. Microbiol. 133:783–791, 1987.
Inoue et al. Nature 205:408–409, 1965.
Mattman et al. "Characteristics of Filterable Forms," Cell Wall Deficient Forms, Stealth Pathogens, chap 24 2nd Edit. pp. 209–216, 289–294, 311–321, 1993.
Nuzum et al. Symposium on Cancer Before Clinical Congress of American College of Surgeons, New York, Oct. 20–26, 1924, pp. 343–352.

*Primary Examiner*—Chris Eisenschenk
*Assistant Examiner*—Manyk Zeman
*Attorney, Agent, or Firm*—Rothwell, Figg, Ernst & Kurz, p.c.

[57] ABSTRACT

Bacteria containing eukaryotic and/or viral genes, and often having highly pleiomorphic morphology, are obtained by culturing virally-infected eukaryotic cells under aseptic, low oxygen conditions. The bacteria so produced express products encoded by the eukaryotic genes. Analyses indicate that several isolates obtained from culturing retrovirally-infected human brain capillary endothelial cells express human-specific genes previously mapped to widely separated human chromosomes.

14 Claims, No Drawings

METHODS FOR THE ISOLATION OF BACTERIA CONTAINING EUKARYOTIC GENES

CROSS-REFERENCE TO RELATED APPLICATION

This application is a continuation-in-part of application Ser. No. 08/261,977, filed on Jun. 17, 1994.

BACKGROUND OF THE INVENTION

1. Field of the Invention

The present invention relates to methods for producing bacteria that contain eukaryotic genes. More specifically, the invention relates to methods for culturing retrovirally-transformed eukaryotic cells under conditions whereby bacteria containing eukaryotic genes subsequently are isolatable from the culture.

2. Description of the Background Art

During the past century, highly pleomorphic bacteria have been isolated from human patients with a variety of illnesses including cancer, acquired immunodeficiency syndrome (AIDS) and Hodgkin's disease.

In the late 19th century, researchers believed that cancer was caused by an infection. But by the 1920's, after numerous microorganisms were isolated and tested for vaccination potential, researchers discovered that the metastasis of cancer can be caused by the spread of cancer cells within the host. Accordingly, the focus of cancer research turned away from isolation of microorganisms.

However, microorganisms continued to be isolated from the blood and tumors of humans and animals with cancer (See Young, *Br. Med. J.* (1925) 1:60; Nuzum, *Surg. Gynecol. Obstet.* (1925) 11:343; Glover, *Canada Lancet Pract.* (1920) 75:92; Glover et al., *Canada Lancet Pract.* (1926) 66:49; Scott, *Northwestern Med.* (1925) 24:162; Stearns et al., *J. Bacterial* (1929) 18:227). These bacteria often showed characteristics of cell wall-deficient bacteria and could be observed in the blood of cancer patients by darkfield microscopy. Cancer appeared to be induced by injecting these bacteria into experimental animals, and some forms of cancer were shown to be prevented by pre-vaccination with killed bacteria isolated from experimental animals affected with the specific cancer.

For example, Diller vaccinated a group of mice with killed bacteria which had been originally isolated from mice with Sarcoma 180; another group of mice was held as unvaccinated controls. All these mice were then challenged with Sarcoma 180. Sixty percent of the bacteria-vaccinated mice rejected the implants after 10 days and lived indefinitely, but all control mice died of their tumors (*Ann. N.Y. Acad. Sci.* (1970) 174:65). Similarly, Seibert vaccinated young, inbred female mice from a strain of mice having a high incidence of breast cancer with heat-killed bacteria isolated from a mouse with breast cancer of this same strain. These mice showed a statistically significant delay in developing this seemingly inherited breast cancer as compared with unvaccinated female controls (*J. Reticuloendothelial Soc.* (1977) 21:279).

The bacteria showed a remarkable tendency toward pleomorphism in culture, sometimes appearing as cocci, sometimes as straight or curved rods, sometimes as motile bacilli, and sometimes mimicking fungi by producing pseudohyphae or larger spore sacs. Some stages of the bacteria could be passed through filters designed to hold back all ordinary bacteria. On culturing these filtrates, the original bacteria would regrow.

Later researchers confirmed and extended these findings (See Wuerthle-Caspe et al., *Ann. N.Y. Acad. Sci.* (1970) 174:636; Alexander-Jackson, *Growth* (1966) 30:199; Diller et al., *Ann. N.Y. Acad. Sci.* (1970) 174:655; Seibert et al., *N.Y. Acad. Sci., Series II* (1972) 34:504; Inoue and Singer, *Nature =1* (1965) 205:408). When sent to reference laboratories for identification, the organisms were classified as common bacteria such as Staphylococcus or Corynebacterium species. But the long time often required for their primary isolation, their sensitivity to the composition of the media, the fried egg appearance of many of their primary isolates, and their marked pleomorphism in culture suggested that their in vivo forms were that of cell wall-deficient bacteria (Mattman, "Cell Wall Deficient Microorganisms", CRC Press: Philadelphia, 1974).

More recently, similar highly pleomorphic bacteria have been isolated from the blood and urine of AIDS patients. AIDS is a complex disease in which patients infected with the human immunodeficiency virus (HIV) experience depletion of CD-4 positive lymphocytes and suffer from an array of opportunistic infections and unusual malignancies. The progressive loss of CD-4 positive T cells and subsequent clinical deterioration correlate directly with increased levels of HIV DNA. Some investigators have attributed loss of control over HIV expression to a number of co-factors, including a variety of heterologous viruses and mycoplasma (Chowdhury et al., *Biochem. Biophys. Res. Commun.* (1990) 170:1365). *Mycoplasma fermentans*, in particular, has been demonstrated in a high percentage of HIV-infected individuals, but the role of the microbe in AIDS is not well defined. Researchers are attempting to link mycoplasma and AIDS (Macon et al., *Human Pathology* (1993) 24:554; Lo et al., Lancet (1991) 338:1415; Wang et al., Lancet (1992) 340:1312). In addition, virus-like infectious agents (VLIA's) have been isolated from AIDS patients which have been shown to cause a systemic infection. These VLIA's are heterogenous in both size and shape (Lo et al., *Am. J. Trop. Med. Hyg.* (1989) 41:364) and have been shown to have a well-defined outer limiting membrane but to lack a cell wall (Lo et al., *Am. J. Trop. Med. Hyg.* (1989) 40:399).

Hodgkin's diseased is yet another malignancy with evidence of infectious causation and perhaps even contagiousness. Cell wall-deficient bacteria have been isolated from patients. Bunting first isolated a certain bacterium from the glands of untreated cases of Hodgkin's disease. The organism was extremely pleomorphic (Bunting, *Bull. Johns Hopkins Hosp.* (1914) 25:173). Later, Mazet isolated 26 strains from Hodgkin's patients which were also extremely pleomorphic (Mazet, *Montpelier Med.* 1941 (1941) 316. Cell wall-deficient ("CWD") bacteria are bacteria which are highly pleomorphic, exhibit poorly developed or absent cell walls, and include not only the mycoplasma, or PPLO's, but also L-form bacteria which have the ability to revert to cell wall producing bacteria in culture. Some CWD bacteria produce a protein resembling chorionic gonadotropin hormone, a substance which appears to protect trophoblastic and cancer cells from immune recognition. There is some evidence that a plasmid may be responsible for this property and even that these bacteria may in some manner be intimately associated with retroviruses. (Macomber, *Medical Hypothesis* (1990) 32:1–9).

Studies of cell wall-deficient bacteria have been hampered by difficulties encountered isolating and culturing them. Specific strains are often difficult to reisolate. In addition, many questions regarding the evolutionary origins of bacteria, cell wall-deficient or not, and their role in human and animal diseases remain unanswered.

SUMMARY OF THE INVENTION

One object of the present invention is to provide novel bacteria containing and expressing eukaryotic genes.

Another object of the invention is to provide a process for producing such bacteria by culturing virus-infected eukaryotic cells under conditions whereby the bacteria subsequently are isolatable from the cell culture.

A further object of the present invention is to provide a process for producing biological products, in particular human biological products, by culturing such bacteria under conditions wherein such products are expressed by the bacteria and are recoverable from the bacterial culture medium.

A further object of the present invention is to provide vaccines derived from such bacteria.

A further object of the present invention is to provide systems for diagnosis and detection of bacteria, retroviruses and retrovirally-mediated diseases comprising antibodies to such bacteria.

A further object of the present invention is to provide expression vectors and/or systems, derived from such bacteria, that express animal or eukaryotic genes.

A further object of the present invention is to provide industrial enzymes and other useful biochemicals derived from such bacteria.

A further object of the present invention is to provide therapeutically useful agents, including antibiotics, derived from such bacteria.

These and other objects, which will become apparent during the following detailed description, have been achieved or are achievable as a result of the inventor's discovery that it is possible to culture virus-infected eukaryotic cells under low oxygen conditions so as to produce bacteria which contain and preferably express animal and/or viral genes.

DETAILED DESCRIPTION OF THE PREFERRED EMBODIMENTS

In a first embodiment, the present invention provides a bacterium containing eukaryotic and/or viral genes. The bacteria of the invention typically are highly pleomorphic, can contain both eukaryotic and viral genes and preferably express at least one eukaryotic gene such that the gene product is recoverable upon culturing the cells. By "eukaryotic gene" it is meant functional genetic information that was present in the eukaryotic cell being cultured and, preferably, which encodes a protein having commercial value and which is expressed by the bacterium. The "eukaryotic gene" present in the bacterium need not be identical to the gene present in the eukaryotic cell. For example, although genes in many eukaryotic organisms contain sequences (such as introns) that do not code for the polypeptide sequence of the product of that gene, and which may not play any role in the normal expression of the gene product, the "eukaryotic gene" present in a bacterium of the present invention need not contain such "non-coding" sequences. Other differences between the gene present in the eukaryotic cell and the gene present in the bacterium, which do not effect the bacterium's ability to express a desired gene product, may exist.

In some physical or morphological aspects the bacteria obtained according to the present invention can resemble bacteria reported to have been isolated from cancer patients and AIDS patients, that is, the so-called pleomorphic or cell-wall deficient bacteria. Specific examples of bacteria obtained according to the present invention include:

| microorganism | ATCC # | ATCC type | protein(s) expressed |
|---|---|---|---|
| 2P | 55589 | Staphylococcus aureus | Human serum albumin (HSA), Pan protein Kinase C (PKC) Basic fibroblast growth factor (bFGF), bFGF receptor (bFGF-R), Platelet derived growth factor (PDGF), PDGF receptor (PDGF-R), Moloney murine leukemia viral p30 (p30) HLA-DS ($\alpha$ chain), $\alpha$-fetoprotein (AFP) Transforming growth factor-$\beta$1 (TGF$\beta$1) |
| 2W | 55590 | Staphylococcus capitis | HSA, PKC, bFGF, bFGF-R, PDGF-AB, PDGF-R, p30, HLA-DS ($\alpha$ chain), AFP, TGF$\beta$1 |
| 1 | 55588 | Micrococcus luteus | HSA, bFGF, bFGF-R |
| 1a | | | HSA, bFGF-R, PDGF-AB |
| 1c | 55592 | Staphylococcus hemolyticus | HSA, PKC, bFGF, bFGF-R, PDGF-AB, PDGF-R, AFP |
| 3 | | | HSA, PKC, bFGF, AFP bFGF-R, PDGF-R, p30, |
| 4 | | | HSA, bFGF, p30 |
| 5 | 55591 | Staphylococcus epidermidis | HSA, PKC, bFGF, bFGF-R, TGF-$\beta$1, AFP, PDGF-AB, p30 |

These bacteria were deposited in accordance with the Budapest Treaty on Jun. 13, 1994, at the American Type Culture Collection, 10801 University Boulevard, Manassas Va. 20110-2209 under the deposit numbers shown above. Additionally, bacteria obtained according to the present invention have been isolated and typed as *Bacillus licheniformis*, a GRAS (generally-recognized-as-safe) microorganism.

The present invention also provides a process for producing bacteria containing at least one eukaryotic (preferably animal and, most preferrably, human) gene. The process of this invention, sometimes called de novo speciation, can be divided into the following stages:

(i) culturing virally-infected eukaryotic cells under low oxygen conditions to produce a bacterium containing a eukaryotic and/or viral gene; and (ii) selecting and replicating at least one such bacterium. Preferably, the low oxygen conditions comprise alternating anaerobic culturing conditions with at least one brief period of exposure to an aerobic or microaerophilic condition. The step of selecting and replicating the bacterium preferably is carried out under standard bacteriological (aerobic) cell culturing conditions. Each of the steps preferably is carried out under aseptic conditions, thereby eliminating or reducing the possibility of contamination.

I. Culturing virally-infected cells under low oxygen conditions to produce bacteria Suitable virally infected eukaryotic cells, such as retrovirally-infected animal cells, can be obtained from a variety of sources including the American Type Culture Collection (ATCC). Alternatively, suitable retrovirally infected cells can be prepared by, for example, infecting an animal cell with a retrovirus using conventional techniques, such as those disclosed by Robinson et al., Blood (1991) 77:294.

The term "animal" as used herein means a yeast cell or a cell isolated from one of the following phyla: Porifera, Coelenterata, Platyhelminthes, Nematoda, Rotifera, Bastrotricha, Mollusca, Annelida, Onychophora, Arthropoda, Echinodermata, Hemichordata, Chordata. These cells are preferably isolated from the phyla Chordata, preferably from mammals, most preferably from humans. Suitable mammalian cells include endothelial cells, including brain capillary endothelial cells, monocyte-macrophages, hepatoma cells and fibroblasts. Endothelial cells are preferred. Brain capillary endothelial cells are particularly preferred, and human brain capillary endothelial cells are most preferred.

Any infectious retrovirus can be used. Preferably a retrovirus such as Moloney murine leukemia virus, L-cell virus, SIV, HIV or Abelson murine leukemia virus is used (see Dickson et al., In "RNA Tumor Viruses: Molecular Biology of Tumor Viruses:, Vol. 1, Weiss et al., Eds, Cold Spring Harbor Laboratory Press; N.Y., 1984). Alternatively, an animal or eukaryotic cell which contains a proviral element can be used. Additionally, DNA viruses or vectors derived therefrom (e.g. SV-40 vector) can be used.

The bacteria according to the present invention are suitably produced in accordance with a preferred embodiment of the invention by incubating retrovirally infected animal cells under low oxygen conditions, such as anaerobic culture conditions with at least one intermittent exposure to aerobic or microaerophilic conditions (hereafter referred to as "alternating anaerobic/aerobic" conditions or "anaerobically/aerobically cultured") in eukaryotic medium such as DMEM, RPMI, F12, F-10, M199, BME (Basal Media eagle), Leibovitz's L-15, Fischer's medium, McCoy's or Weymouth's medium, or in the cell culture medium described in the Examples that follow. The alternating anaerobic/aerobic incubation typically is conducted for at least 24 hours, preferably 24–72 hours, at 20–50° C., preferably 30–40° C., most preferably at about 37° C. Suitable bacteriological medium (in which the cells are cultured using standard bacteriological cell culture conditions following the anaerobic/aerobic culturing step, as described herein) includes Staphylococcus Medium 110 Agar, a concoction of sunflower seeds, Iceland moss, Irish moss (See Glover, *Can. Lancet Pract.* (1930) 75:92); 3:1 ascitic fluid: nutrient agar (see Nuzum, *Surg. Gynecol. Obstet.* (1925) 11:343), Brain Heart Infusion, Bromthymol Blue Lactose Agar, Dubos Medium, Dextrose Blood Agar, Peptone-Yeast Extract Broth, Staphylococcus Broth, PPLO Media with or without Crystal Violet, Mannitol Salt Agar, Thioglycolate Medium, Brewer Modified, Peptone Glucose Yeast Extract Agar, Phenol Red Mannitol Agar, Phenylethanol Blood Agar, Sheep's Blood Agar, Mannitol Salt Broth, Luria-Bertani Broth, and Trypticase Soy Broth.

Suitable anaerobic conditions include an atmosphere of 0–2 v/v % oxygen, preferably 0–1 v/v % oxygen, most preferably less than 0.1 v/v % oxygen, most preferably 0 v/v % oxygen. The anaerobic atmosphere is typically an inert gas such as $N_2$ or Ar. Suitable aerobic conditions typically include an atmosphere containing more oxygen than the atmosphere used for anaerobic culturing, for example, air with 5% carbon dioxide, an atmosphere of air, or an atmosphere containing up to about 21 v/v % oxygen.

II. Selection and Replication of Bacteria

After alternating anaerobic/aerobic culturing, the medium (or cells therefrom) is cultured under conditions supporting the growth and replication of bacteria, such as standard bacteriological cell culturing conditions. For example, the medium containing the cells subjected to the anaerobic/aerobic culturing step, or cells obtained therefrom, are aerobically incubated at a temperature between about 4 and 50° C., preferably at 20–40° C., for at least 24 hours, preferably for several days and most preferably for several weeks. In this context, "aerobically incubated" means culturing in an atmosphere containing greater than 2 v/v % $O_2$, preferably greater than 5 v/v % $O_2$. Good results can be obtained by culturing in air.

In one embodiment, the medium containing eukaryotes and eukaryotic debris from the anaerobic/aerobic culturing step is resuspended, diluted and re-cultured aerobically. Any conventional medium suitable for culturing bacteria can be used including Mannitol Salt Agar, Staphylococcal Medium, Brain Heart Infusion, Bromthymol Blue Lactose Agar, Dubos Medium, Dextrose Blood Agar, Peptone-Yeast Extract Broth, Staphylococcus Broth, PPLO Media with or without Crystal Violet (Growth is tolerated by any enrichment medium. However, high-salt media tolerate growth of L-forms and mostly Staphylococcus species.), Mannitol Salt Agar, Thioglycolate Medium, Brewer Modified, Peptone Glucose Yeast Extract Agar, Phenol Red Mannitol Agar, Phenylethanol Blood Agar, Sheep's Blood Agar, Mannitol Salt Broth, Luria-Bertani Broth and Trypticase Soy Broth. The medium can be the same or different from the medium used during the anaerobic/aerobic eukaryotic cell culturing step.

Alternatively, the anaerobically/aerobically cultured media containing eukaryotic cells is first filtered prior to the aerobic (or "bacteriological") culturing step. Conventional techniques can be used to filter the media such as those described by Mattman ("Cell Wall-Deficient Forms: Stealth Pathogens", 2nd. ed., CRC Press: Boca Raton, Fla., 1993. See ch. 24 in particular). The media is suitably filtered through a 0.1–0.8 $\mu$m filter. Suitable filters include membranes, diatomaceous earth, porcelain, asbestos and sintered glass. Membrane filters are preferably used. The filtrate is then transferred to the bacteriological culture media described above.

Depending on the porosity of the filter, various forms of bacteria can be isolated. For example, to isolate cell wall-deficient bacteria, the anaerobically/aerobically cultured media is first filtered through a 0.20–0.45 $\mu$m filter, preferably a 0.22 $\mu$m filter. Bacteria with cell walls may be obtained by using a filter with a larger pore size.

The present invention also provides a method for producing biological products by culturing the bacteria produced by the present process. The bacteria of the present invention can be used to produce recoverable quantities of biological products that are "coded for" by eukaryotic genes, such as cytokines and receptors (such as interleukin 1–10 and interferons, and their receptors), growth factors and receptors (such as epidermal growth factor (EGF), acid fibroblast growth factor (aFGF), basic fibroblast growth factor (bFGF), platelet-derived growth factor AA, AB, and BB(PDGF AA, AB and BB), insulin-like growth factor (IGF), transforming growth factor (TGF) and their receptors, human serum albumin, alpha-fetoprotein, immunoglobulins, hematopoietic growth factors (such as GM-CSF, G-CSF, etc.), coagulation factors, complement factors, steroid hormones and their receptors (such as glucocorticoid hormones, mineralocortical hormones, sexual steroid hormones, etc. and their receptors), matrix proteins (such as fibronectin, collagen, vitronectin, etc.), other bioactive peptides (such as adrenocorticotropic hormone and fragments, angiotensin and related peptides, atrial natriuretic peptides, bradykinin and related peptides, chemotactic peptides, dynorphin and related peptides, endorphins and β-lipotropin fragments, enkephalin and related peptides, enzyme inhibitors, gastrointestinal peptides, growth hormone releasing peptides, luteinizing hormone releasing hormone and related peptides, melanocyte stimulating hormone and related peptides, neurotensin and related peptides, opioid peptides, oxytocin, vasopressin, vasotocin and related peptides, parathyroid hormone and fragments, protein kinase related peptides (including PKC), somatostatin and related peptides, and substance P and related peptides (such as isoleucine, threonine, tryptophan, etc.).

The bacteria of the present invention can be screened to identify and select for the production of specific biological products, using conventional techniques. For example, commercially available antibody probes can be used to screen these microorganisms. Suitable antibodies are conventionally available from such sources as Sigma Chemical Co (St. Louis, Mo.) and ICN Biomedical (Irvine, Calif.). Other techniques for identifying and/or selecting bacteria of the present invention based upon the nature of the eukaryotic gene product expressed will be apparent. For example, bacteria which overproduce an amino acid can be isolated by culturing the cells, following the low oxygen culturing step, in a medium containing inhibitory concentrations of that amino acid.

The bacteria of the present invention can also be used to understand the interrelationships between complex human gene clusters. Several of the bacteria produced by the present invention express gene products which are known to be located on several different chromosomes. Bacteria which contain genes clusters provide a unique opportunity to study the function and effect of various stimuli on the gene clusters in an organism with smaller genome than the human genome.

In a fourth aspect, the bacteria of the present invention can also be used to generate vaccines against retroviruses or other viruses. Because the bacteria can contain both animal and viral genes, the microorganisms can be used as a "modified" form of the virus to raise an immune response against the virus in a host animal. Conventional techniques can be used to generate live vaccines using the bacteria. Alternatively, the bacteria can be destroyed and used to formulate killed vaccines using conventional techniques. In yet another embodiment, polypeptides or fragments thereof from bacteria can be isolated and formulated into synthetic vaccines using conventional techniques. Conventional techniques for preparing vaccines can be used such as those described in New *Generation Vaccines* (Woodrow and Levine, Eds., Marcel Dekker, Inc.: New York, 1990).

In this aspect of the invention, a retrovirally-infected animal cell which is anaerobically/aerobically cultured is preferably an animal cell from the phyla Chordata, most preferably either avian, fish or mammalian. Useful vaccines are most preferably generated against bovine, porcine, feline, human, canine, equine, avian and fish diseases. For example, vaccines against Staphylococcus infections in cattle can be formulated and vaccines against feline infectious viruses (such as feline infectious leukemia) can be generated.

In yet another embodiment, the bacteria of the present invention can be used to provide systems for the diagnosis and detection of bacteria, retroviruses and retrovirally-mediated diseases comprising antibodies to the bacterial and/or retroviral antigens. Suitable antibodies, including both monoclonal and polyclonal antibodies, can be prepared according to conventional techniques using the bacteria, fragments thereof, or products therefrom as antigen. Suitable techniques are described in Antibodies: A Laboratory Notebook (Harlow, E. and Lane, D., Cold Spring Harbor Laboratory, Cold Spring Harbor, N.Y., 1988).

The bacteria of the present invention also can be used to provide expression systems or expression vectors for the production of various animal or eukaryotic proteins for both therapeutic and diagnostic purposes. Background and suitable techniques are described in Plasmids: A Practical Approach (Second Edition, Hardy, K. G., IRL Press, Oxford, 1993) and Genetic Engineering of Microorganisms (Puhler, A., VCH Verlagsgesellschaft, Weinheim, 1993).

In addition to the biological products described above, the bacteria of the present invention can be used to provide industrially useful biological molecules, such as enzymes. "Industrial" or "bulk" enzymes include amylases, cellulases, lignocellulose-degrading enzymes, pectinases, proteases, and ligases. Bacterial sources and applications of these enzymes are described in Protein Biotechnology (Walsh, G. and Headon, D., Wiley, Chichester, 1994).

The bacteria of the present invention also can be used to provide antibiotics. Bacteria of the genus Bacillus produce antibiotics such as bacitracin and polymyxin. Actinomyces of the genus Streptomyces produce antibiotics such as streptomycin, chloramphenicol, tetracycline, and erythromycin. The microbiology of these bacteria is described in Biology of Microorganisms (Brock, T. D., Smith, D. W., and Madigan, M. T., Prentice-Hall, 1984).

Having generally described this invention, a further understanding can be obtained by reference to certain specific examples which are provided herein for purposes of illustration only and are not intended to be limiting unless otherwise specified.

EXAMPLES

Example 1

Gelatinized culture flasks containing $5-6 \times 10^7$ RT-HCMV endothelial cells (grown to confluence aerobically) are incubated anaerobically in 50 ml of medium consisting of 1:1 proportions of Medium 199 and Ham's F12 containing 80 mM DMSO (tissue culture grade), 11 mM fructose, 35 mM succinate, and 800 mg/L glutamate. In the first anaerobic phase, anaerobic conditions are prepared by flushing the medium with nitrogen for 10–15 minutes prior to cell incubation. Cultures fed with anaerobic medium are then placed in an anaerobic jar (obtained from Becton Dickinson and modified so as to have both a gas inlet and a gas outlet). The gas line into the anaerobic jar is connected to a 0.20 μm sterile filter in order to filter out possible microbial contaminants in the nitrogen gas reservoir or the gas line. The anaerobic jar, containing the sterilely vented culture flasks with eukaryotic cells, is sealed and periodically flushed with sterile nitrogen gas for 2–3 hours until the effluent gas contains 0% oxygen as measured by an oximeter (available from Teledyne) to ensure an anaerobic atmosphere. The anaerobic jar gas lines are then clamped tightly and the jar is placed for approximately 18–24 hours in a cell incubator set at a temperature of 30° C.

After 18–24 hours, the anaerobic jar is taken from the cell incubator. The jar is opened to the atmosphere and the sterilely vented culture flasks are quickly sealed to prevent exposure to aerobic conditions. Each flask is examined under a tissue culture microscope at room temperature in a well-lit (fluorescent lighting) laboratory. After 1–2 hours, medium samples of 2–3 ml are aspirated from each flask under sterile conditions for further microscopic examination, thus briefly exposing the flask contents to aerobic (microaerophilic) conditions. The sterilely vented culture flasks are placed in the anaerobic jar, which is flushed with sterile nitrogen gas as described previously. During this reinstitution of anaerobic conditions, the culture flask contents are exposed to aerobic or, more probably, microaerophilic conditions. This procedure is repeated after another 18–24 hours.

After approximately 72 hours of alternating anaerobic/aerobic incubation as described above, the RT-HCMV endothelial cell suspensions are filtered through sterile, 0.22 um Millipore filters (available from Millipore, Bedford, Mass.) in order to exclude eukaryotes and any cell-walled bacteria. Filtrates are plated onto Mannitol Salt Agar (MSA) medium or Staphylococcal Medium 110 Agar and incubated in air at 37° C. After several days, distinct colonies appear on the plates. For the isolation of *Micrococcus luteus*, a 0.8 $\mu$m sterile filter is used to exclude eukaryotes prior to aerobic bacteriological culturing.

Comparative Example 1/A

Controls containing medium only are treated in the same manner as Example 1. No microbial growth is observed following the aerobic bacteriological culturing of medium from these control flasks.

Comparative Example 1/B

In order to determine whether or not "overt" microbial contamination existed in the RT-HCMV endothelial cell line, RT-HCMV endothelial cells are cultured directly into a variety of bacteriologic media. These media include Trypticase Soy Broth, Staphylococcus Broth, and the standard medium used to culture RT-HCMV endothelial cells. Cultures are incubated in a shaker, aerobically, and at 37° C. After 24 hours, aliquots of all three liquid cultures are plated onto Staphylococcal Medium 110 agar, incubating the plates in air and at 37° C. After 10 days, no growth is observed on these plates. After 72 hours and without observing any gross bacterial growth in the liquid cultures, the Staphylococcus Medium 110 culture is filtered through 0.22 um Millipore filters, and the filtrates are plated onto staphylococcus medium 110 agar plates. After incubating for eight days in air at 37° C., no bacterial growth is observed on any of these plates.

In addition, RT-HCMV endothelial cells are cultured aerobically in the medium used for the anaerobic incubation of RT-HCMV endothelial cells, and in PPLO broth with Bacto Mycoplasma Supplement S for 14 days. These cultures are maintained in conditions suitable for the aerobic isolation of mycoplasmas (10% $CO_2$; 35° C.), common "contaminants" of cultured eukaryotic cells (Animal Cell Culture: A Practical Approach, Second Edition, Freshney, R. I., Ed., IRL Press, Oxford, 1992). Isolating no mycoplasmas in this manner, a highly sensitive, double-step-PCR molecular phylogenetic method using nested, degenerate primers is used to detect gene sequences coding for the evolutionary conserved 16 S rRNA of some 25 different mycoplasma species including those most commonly found in cell cultures (Hopert et al, J. Immunol. Meth. (1993) 164:91). The predicted mycoplasma 16 S rRNA gene sequence from positive control samples, *Mycoplasma fermentans* (ATCC 19989) and *Mycoplasma pirum* (ATCC 25960) DNA is amplified. No mycoplasma 16 S rRNA gene sequences from the DNA of aerobically cultured cells lines/strains, including non-transformed human and porcine cerebral microvascular endothelial cells, and L cell-virus transformed human (RT-HCMV) and porcine (RVTE) cerebral microvascular endothelial cells, are amplified. Further phylogenetic analyses of mycoplasma 16 S rRNA's through Genbank indicate that the PCR primers/method should detect corresponding mycoplasma 16 S rRNA gene sequences from the DNA of any anaerobic mycoplasma(s) which might be dormant in aerobically cultured RT-HCMV endothelial cells.

These experiments indicate that the bacterial isolates are not contaminants in actively propagating RT-HCMV endothelial cells cultures. The experiments rule out the possibility that contamination of RT-HCMV endothelial cells occurred coincidentally, thus demonstrating the importance of the subject process for deriving the bacteria.

Comparative Example 1/C

The RT-HCMV endothelial line is subjected to rigorous sterility and mycoplasma testing in order to exclude the possibility that the cell line harbors bacterial, fungal or mycoplasma contaminants. The methods for bacterial and fungal sterility testing meets or exceeds USP XXII and/or 21 C.F.R. § 58 requirements. The mycoplasma assay tests for the presence of agar-cultivable and non-cultivable (Vero cell assay) mycoplasma. The sterility and mycoplasma assays employed are similar to those described in Animal Cell Culture: A Practical Approach, Second Edition (Freshney, R. I., Ed., IRL Press, Oxford, 1992). The RT-HCMV endothelial cell line is found to be negative for the presence of bacterial, fungal or mycoplasma contaminants.

Comparative Example 1/D

Human brain capillary endothelial cells are transformed with the L cell virus, a murine retrovirus closely related to the Moloney murine leukemia virus, using techniques similar to those used for the establishment of retrovirally transformed porcine cerebral microvascular endothelial cell lines (Robinson et al., *Blood* (1991) 77:294) tb produce retrovirally transformed human capillary microvascular (RT-HCMV) endothelial cells. The cells are available from the American Type Culture Collection, Manassas, Va., USA, under accession number ATCC CRL 11655. RT-HCMV cells are grown to confluence in gelatinized tissue culture flasks with an atmosphere containing air with 5% $CO_2$ and at a temperature of 37° C.

Subsequently, culture flasks containing $5-6 \times 10^7$ RT-HCMV endothelial cells are subjected to various concentrations of sodium chloride, dimethylsulfoxide or hydrogen sulfide added to standard culture medium and incubated under aerobic conditions (without fluctuations of oxygen concentrations) at temperatures between 30–37° C. The cultures are examined daily for up to one week for any signs of microbial outgrowth. In addition, eukaryotic cell samples subjected to these conditions are examined by electron microscopy. No bacteria are isolated from these experiments.

Comparative Example D

RT-HCMV endothelial cells are cultured in medium 199 supplemented with 100 pg heparin/ml, 2 mM L-glutamine, and 10% heat-inactivated fetal bovine serum (FBS). Prior to seeding, all cell culture flasks are pretreated for 15 minutes (followed by a lx PBS wash) with 1% gelatin (2% sterile gelatin solution from Sigma diluted with an equal volume of sterile tissue culture grade water). Twelve T-75 flasks with standard (no filter) caps at passage 6 are used. Each flask contains approximately $2.23 \times 10^7$ viable (trypan blueexcluding) cells/flask. Medium is aspirated from six of the flasks, and each of these flasks is re-fed with sterile nitrogen ($N_2$)-flushed medium and Ham's/F12 (1:1 proportions supplemented with 80 mM DMSO, 11 mM fructose, 25 mM succinic acid, 800 mg L-glutamic acid, and 100 ug heparin/ml. All medium is filtered using a Corning 0.22 µm sterile filter unit. Prior to feeding, the medium is flushed with sterile nitrogen gas for 10–15 minutes. One flask without cells containing sterile $N_2$-flushed growth medium is used as a medium control flask. The seven flasks are transferred to the anaerobic chamber, and the chamber is sealed and purged with sterile-filtered $N_2$ four times over approximately a two hour period for a total flush time of approximately one hour. The air in the chamber is analyzed for oxygen concentration with a Fryrite analyzer until the $O_2$ level reads 0% for at least two consecutive Fryrite $O_2$ tests. The tubing to the chamber is clamped off and the chamber is placed for approximately 72 hours in an incubator at 36° C. ±2° C.

Six control flasks are aspirated and re-fed with the same growth medium (25 ml/flask), which is not flushed with $N_2$. One flask (with no cells) containing medium only is included as a medium control flask. These seven flasks are incubated aerobically for approximately 72 hours at 36° C. ±2° C. in the same incubator that houses the experimental chamber.

Approximately 24 and 48 hours after initiation of the experiment, the chamber is opened at room temperature in a well-lit room, and the flask caps are quickly sealed. The flasks are observed microscopically and the observations are recorded. These observations are performed within 10 minutes. The flasks are then placed unstacked in a laminar flow hood under fluorescent light for approximately 30 minutes. After 30 minutes, the caps are loosened, and the flasks remain in the hood for another 2–3 minutes.

The flasks are then transferred to the experimental anaerobic chamber, which is sealed and flushed with sterile $N_2$ until the effluent gas measures 0% oxygen. The tubing to the chamber is clamped off, and the chamber is placed back into the incubator. The control flasks are manipulated in a similar manner and returned to the incubator.

After 72 hours incubation, the chamber and control flasks are removed from the chamber. The contents from each experimental flask are scraped and vigorously mixed and aspirated several times with a 10 ml pipet for approximately 2 minutes, followed by vortexing for approximately 2 minutes. The contents from the experimental flasks are pooled, and the samples are collected for sterility and mycoplasma assays. The remainder of these pooled samples are then sterile filtered through a 0.22 um filter, and the filtrate samples are collected for sterility and mycoplasma assay. The control cell flasks are treated in the same manner, and the samples are collected for sterility and mycoplasma testing. The remainder of the control material is filtered through a 0.22 um filter, and the filtrate is collected for sterility testing. A duplicate experiment using procedures similar to those described above is performed.

One part of the bacteriological culture phase of the process involves plating both experimental and control samples on mannitol salt agar (MSA), Staph 100 (S100) agar, or blood agar (BDL), followed by incubation at 36° C. ±1° C. for 14–21 days. Another part of the bacteriological culture phase involves extensive sterility tests (aerobic and anaerobic) with both positive and negative controls. Positive controls include *Bacillus subtilis, Bacteroides vulgatus, Staphylococcus aureus,* and *Candida albicans.* These sterility tests meet or exceed USP XXIII and/or 21 C.F.R. § 610 requirements.

The mycoplasma tests (aerobic and anaerobic) are designed to detect both agar-cultivable and non-cultivable mycoplasmas in large sample volumes using two test systems: agar isolation and Hoescht staining of Vero (monkey kidney) cells inoculated with experimental and control samples together with positive and negative mycoplasma controls. The sterility and mycoplasma assays employed are similar to those described in Animal Cell Culture: A Practical Approach, Second Edition (Freshney, R. I., Ed., IRL Press, Oxford, 1992).

After one to several weeks of incubation, five Gram-positive rods are isolated from the bacteriological cultures of experimental eukaryotic cell samples subjected to anaerobic eukaryotic cell culture conditions with periodic introductions of an aerobic atmosphere during the eukaryotic cell culture phase. Four different colony morphologies are observed. All isolates are typed as *Bacillus licheniformis*. All eukaryotic cell controls (aerobic culture only) and media controls (aerobic and anaerobic/aerobic culture) are negative for bacterial outgrowth during bacteriological culturing. These experiments indicate that the bacteria are evolved de novo from eukaryotic cells.

Comparative Example 2/A

Two experiments are performed in which RT-HCMV cells are subjected to approximately 72 hours of anaerobic conditions in the experimental anaerobic chamber without the periodic introduction (or reintroduction) of an aerobic atmosphere during the eukaryotic cell culture phase. Eukaryotic cell controls (aerobic only) and media controls (aerobic and anaerobic only) are performed in tandem. No bacteria or mycoplasmas are isolated from the bacteriological cultures of experimental and control samples.

Example 3

In order to determine the further filterability of these bacteria, the isolate, *Micrococcus luteus*, obtained in Example 1 after filtration through a 0.8 µm filter is returned to the same initial alternating anaerobic/aerobic culture conditions used for its isolation from RT-HCMV endothelial cells. After 72 hours, the bacterial cell suspension is filtered through a 0.22 µm Millipore filter, plated onto MSA, and incubated in air at 37° C. Within several days, colonies of bacteria are observed growing on MSA. One of these colonies is classified as a *Staphlococcus hemolyticus.*

Example 4

To demonstrate that the isolation of bacteria is not peculiar to the RT-HCMV endothelial cell system, actively propagating cultures of retrovirally transformed porcine cerebral microvascular endothelial cells (Robinson et al., *Blood* (1991) 77:294), L929 cells (ATCC CCL 1) and murine lymphoma cells (ATCC TIB52) are treated in the manner as described above in Example 1. Gram-positive bacteria are isolated from the cultures originally containing retrovirally transformed porcine cerebral microvascular endothelial cells. In L929 cells transformed with another murine retrovirus, gram-positive bacteria are observed in Staphlococcus Broth within 24 hours of inoculation from an anaerobic/aerobic experiment. In the murine lymphoma cells transformed with the Abelson MuLV, gram-positive bacilli are obtained.

Comparative Example 4/A

In order to determine whether or not the presence of an infectious virus is integral to this process, similar experiments are performed with two other transformed cell lines, an SV40-transformed human colon cell line (ATCC CRL 1807) and a human colon adenocarcinoma cell line (ATCC HTB 38; HT-29 cells). Example 1 is repeated using these cell lines in place of the RT-HCMV endothelial cells. Two gram-positive cocci and one gram-positive bacillus are isolated from SV40 cells during the bacteriological culturing phase. No bacteria are isolated from the human colon adenocarcinoma cell line.

Example 5

Characterization of the Bacteria

A. Morpholoay

As nine bacterial isolates are filtered through a 0.20 or a 0.22 um Millipore filter prior to plating on solid media, by definition, they exhibit an L-form or cell wall deficiency during some phase of their life cycles (Mattman, "Cell Wall-Deficient Forms: Stealth Pathogens", 2nd. ed., CRC Press: Boca Raton, Fla., 1993). Based on MSA and carbohydrate fermentation patterns, these isolates are categorized into three groups, designated I, II, and III.

Five of these bacterial isolates were subjected to extensive bacteriologic analyses at the ATCC. Individual isolates were classified as Micrococcus luteus (isolate 1; Group III), *Staphylococcus aureus* (isolate 2P; Group II), *Staphylococcus epidermidis* (isolate 5; Group I), *Staphylococcus hemolyticus* (isolate 1c; Group II). A gliding motility was documented in some strains. In addition, several strains grew well on PPLO agar exhibiting a classic "fried egg" C.olony morphology.

Another five bacteria derived with the subject process were classified as different isolates of *Bacillus licheniformis*, a GRAS microorganism. Filtration is not performed prior to the bacteriological culturing phase in the production of these bacteria.

Morphology studies of the isolates with light microscopy revealed an ultrastructure that was extremely pleiomorphic. In the case of the staphylococcal isolates, the bacteria exhibit a fairly uniform coccoid morphology when cultured in Staphylococcal Broth. In many samples examined, abundant extracellular material is present. Morphologies that appear to be of neither a prokaryotic nor a eukaryotic nature were often observed in culture in Staphylococcal Broth. When cultured in the standard medium used for the culture of RT-HCMV endothelial cells, i.e. with a low salt concentration, various bizarre morphologies were often observed.

B. Presence of Retroviral DNA

The presence of the retroviral DNA in the bacterial isolates, derived as described in Example 1, was demonstrated by PCR amplification of a 500 bp portion of the retroviral gag gene. The L cell virus gag gene is detected by PCR analysis of L929 cell DNA with primers designed to amplify a 500 bp fragment of the Moloney MuLV gag gene followed by restriction enzyme analysis.

RT-HCMV endothelial cell DNA and isolate 2P ("*Staphylococcus aureus*") DNA are analyzed via PCR primers designed to amplify a 500 bp fragment of the Moloney MuLV gag gene followed by restriction enzyme and analysis. Using the published sequence of the Moloney MuLV (Shinnick et al., *Nature* (1981) 293:543), the following PCR oligonucleotide primers are synthesized: upstream, bp 1561 to bp 1585; downstream, bp 2057 to bp 2035. PCR conditions per reaction include the use of 1× Taq polymerase buffer (BRL), 2.0 mM $MgCl_2$, 200μM dNTPs (Perkin Elmer), 1 ug each primer, 0.5 units Taq polymerase (BRL), and 2 ug genomic DNA. Cycling parameters are as follows: 40 cycles of 95° C. for 40 seconds followed by 55° C. for 1 minute, 72° C. for 1 minute, and a final extension at 72°° C. for 10 minutes. PCR products are electrophoresed on a 3.0% agarose gel (Perkin Elmer) and 500 bp products are isolated using GeneClean (Bio 101). One ug of each purified product is restricted with either MspI (BRL) or BglII (BMB). Selection of the restriction enzymes, MspI and BglII, for analysis of the 500 bp gag gene PCR products is based on a Moloney MuLV restriction map. Restriction fragment sizes correspond to those predicated by a Moloney MuLV restriction map.

Using western blot, RT-HCMC endothelial cells are shown to express the gag p30 core protein. Isolate 2P expresses significant amounts of the p30 core protein and related proteins. Isolate 2W expresses small amount of p30 core protein with an apparent faster electrophoretic mobility, a previously documented physicochemical trait of the p30 core protein (Dickerson et al, 1984). Other CWD microorganisms isolated from the cultures also express p30 core protein.

For immunoblotting equal amounts of protein from RT-HCMV endothelial cells, isolates 2P and 2W, the two historical cancer-related microbes, and the *Staphylococcus aureus* Woods strain 46 were loaded on a SDS-PAGE gel. After gel electrophoresis and transfer to a polyvinylidene difluoride membrane (BIO-RAD), the blot is probed with a 1:500 dilution of antisera raised against the Moloney MLV gag p30 core protein. Detection is performed with an alkaline phosphatase method.

C. Presence of animal DNA, animal genes, And animal gene products or proteins

Subsequently, all isolates were screened for the presence of human gene products using western blotting or indirect fluorescent immunochemistry. Antibodies used to analyze the microbes include those directed against human serum albumin (HSA), protein kinase C (PKC), basic fibroblast growth factor (bFGF) and its receptor, and platelet-derived growth factor dimers AB (PDGF-AB), the PDGF receptor, α-fetoprotein, transforming growth factor-$β_1$ and HLS-DS (α chain). For western blotting equal amounts of protein from RT-HCMV endothelial cells, CWD bacteria 2P and 2W and several other isolates, the two historical cancer-related microbes, and the staphylococcal protein A-negative staphylococcus control were loaded in each lane. The microorganism described by Livingston-Wheeler et al. (in "The Microbiology of Cancer: Compendium", Livingston Wheeler Medical Clinic Publication: San Diego, 1977), which was isolated from a patient with metastatic cancer, produces an HCG-like protein and is identified by the ATCC as a *Staphylococcus hemolyticus* (ATCC 43253). The microorganism described by Seibert et al. (*Ann. N.Y. Acad. Sci.* (1970) 174:690), which was directly isolated from breast adenocarcinoma tissue, also produces an HCG-like protein, and is identified by the ATCC as a *Staphylococcus warneri* (ATCC 25614). The *Staphylococcus aureus* Woods strain 46 (ATCC 10832) (Miele et al., *Am. J. Vet. Res.* (1981) 42:2065) is used as a staphylococcal protein A-negative control. After gel electrophoresis and transfer to polyvinylidene difluoride (PVDF) membranes, blots are probed with specific antibodies. Detection is performed with an alkaline phosphatase method.

Western blots for both protein kinase C and PDGF using protein pellet samples extracted from several of the isolates, two historical, cancer-related microorganism controls, and a staphylococcal protein A(SPA)-negative *Staphylococcus aureus* Wood strain 46, as a control for the SPA pseudo-immune Fc reaction (Miele et al., *Am. J. Vet. Res.* (1981) 42:2065) are performed. Equal amounts of total protein are placed in each lane for SDS-PAGE electrophoresis and then transferred to a PVDF membrane. The membranes are then probed by the respective polyclonal antibodies that recognize pan PKC, m.w. 77–85 kDa, and PDGF-AB dimers, m.w. 28–34 kDa (UBI, Lake Placid, N.Y.). The presence of these proteins is observed in several or more of the isolates.

Isolate 2W expressed pan PKC (approx. m.w. 80 kDa) in significant amounts. Little, if any PKC was detected in Group III by western blotting indicating a "subspecies" variation in either genomic content or gene expression. Isolate 2P appeared to produce significant amounts of PDGF-AB dimers (approx. m.w. 28–34 kDa) even when compared to the positive control. As in the previous observation concerning p3O core protein expression, the *Staphylococcus warneri* isolated by Seibert et al. appears to produce recombinant forms of PKC and PDGF.

HSA is also detected in some of the CWD (staphylococcal) bacteria by immunoblotting. The pellet protein sample from isolate 1C contained the 63 kD form of HSA and related polyproteins and degraded protein. The supernatant protein sample contained the 63 kD form and a significant amount of the 66 kD form. To confirm the presence of the HSA gene (cDNA form) in isolate 1C, PCR and restriction enzyme analysis of a 1.95 kb HSA cDNA fragment sequence from isolate 1C genomic DNA (Watkins et al., *Proc. Nat'l Acad. Sci. USA* (1991) 88, 5959) was employed. The cDNA form of the HSA gene was found in the genome of isolate 1c (*Staphylococcus hemolyticus*).

The presence of human serum proteins was documented in one isolate classified as *Bacillus licheniformis*. Using indirect fluorescence immunocytochemistry and a polyclonal anti-human serum protein antiserum (Sigma), this isolate exhibits a four-plus immuno-fluorescence, whereas a control *Bacillus licheniformis* (source: ATCC) exhibits a zero-to-one-plus immunofluorescence. Thus, this indirect fluorescence immunocytochemical technique documents the presence of expressed human serum proteins in an isolate of *Bacillus licheniformis* derived with the subject process.

Finally, the human eukaryote-derived Alu and LINES inter-repeat elements are found in genomic DNA samples from isolates 2P and 2W using the polymerase chain reaction (PCR) technique. Gel electrophoresis DNA smears typical of inter-repeat element amplification are observed when using human placenta, RT-HCMV endothelial cells, and isolates 2P and 2W genomic DNA samples but are absent when using porcine genomic DNA samples as negative controls. Therefore, the presence of multiple gene products for several human genes previously mapped to widely separated chromosomes (Nierman et al, *ATCC/NIH Repository Catalogue of Human and Mouse DNA Probes and Libraries*, American Type Culture Collection: Rockville, Md., 1992) and the presence of "human" inter-repeat elements indicate that the genomes of the bacteria derived with the present invention are evolved from the human genome.

Having now fully described the invention, it will be apparent to one of ordinary skill in the art that many changes and modifications can be made thereto without departing from the spirit or scope of the invention as set forth herein.

I claim:

1. A method for isolating a bacterium, comprising:

(a) preparing a culture of retrovirally transformed human capillary microvascular endothelial cells, ATCC CRL 11655, in an aseptic, eukaryotic cell culture medium, (b) subjecting the culture of step (a) to an anaerobic culturing phase under aseptic conditions wherein the culture is subjected to anaerobic culturing conditions corresponding to an atmosphere of about 0 to about 2 v/v % oxygen, for a period of time of between about 18 and 24 hours, followed by (c) exposing the culture under aseptic conditions to oxygen conditions corresponding to an atmosphere containing greater than about 2 v/v % oxygen, (d) subjecting the culture to an additional anaerobic culturing phase under aseptic conditions wherein the culture is subjected to anaerobic culturing conditions corresponding to an atmosphere of about 0 to about 2 v/v % oxygen, for a period of time of between about 18 and 24 hours, (e) subjecting the culture of step (d) to an aerobic culturing phase under aseptic culturing conditions and corresponding to an atmosphere containing greater than about 2 v/v % oxygen in a bacterial culturing medium, and (f) isolating from the culture of step (e) a bacterium selected from the group consisting of *Staphylococcus aureus*, ATCC 55589; *Staphylococcus capitis*, ATCC 55590; *Staphylococcus hemolyticus*, ATCC 55592; *Staphylococcus epidermidis*, ATCC 55591; *and Micrococcus luteus*, ATCC 55588.

2. The method according to claim 1, wherein said anaerobic culturing step (b) is carried out in an atmosphere containing less than or equal to about 0.1 v/v % oxygen, based on the total volume of atmosphere.

3. The method according to claim 2, wherein said anaerobic culturing step (b) is carried out in an atmosphere containing less than or equal to about 1 v/v % oxygen, based on the total volume of atmosphere.

4. The method according to claim 1, further comprising filtering the cells cultured in step (a) prior to said step (b).

5. The method according to claim 4, comprising filtering the cells through a 0.1 to 0.8 µm filter.

6. The method according to claim 5, wherein the filter is 0.1 to 0.45 µm.

7. The method according to claim 5, wherein the filter is 0.22 µm.

8. The method according to claim 1 comprising repeating steps (c) and (d) at least once, prior to carrying out step (e).

9. The culture designated ATCC 55589.

10. The culture designated ATCC 55590.

11. The culture designated ATCC 55588.

12. The culture designated ATCC 55592.

13. The culture designated ATCC 55591.

14. The culture designated ATCC CRL 11655.

* * * * *